US00PP35112P2

(12) United States Plant Patent
Berry

(10) Patent No.: US PP35,112 P2
(45) Date of Patent: Apr. 18, 2023

(54) ***LAGERSTROEMIA* PLANT NAMED 'JBG 19003'**

(50) Latin Name: *Lagerstroemia indica*
Varietal Denomination: JBG 19003

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 17/875,366

(22) Filed: Jul. 27, 2022

(51) Int. Cl.
*A01H 6/00* (2018.01)
*A01H 5/02* (2018.01)

(52) U.S. Cl.
USPC ..... Plt./252

(58) Field of Classification Search
USPC ..... Plt./252
CPC ..... A01H 6/00; A01H 5/02
See application file for complete search history.

*Primary Examiner* — Keith O. Robinson
(74) *Attorney, Agent, or Firm* — Weatherly IP Solutions, LLC

(57) ABSTRACT

A new cultivar of *Lagerstroemia* named 'JBG 19003' that is distinguishable by a compact plant habit, a form which is upright initially, becoming weeping or cascading when established and planted in the landscape, red flowers, foliage which is very dark brown to black in summer and red-brown in color in the fall, is very well-adapted to heat, humidity and drought conditions, and exhibits slight or occasional susceptibility to aphids, whitefly and powdery mildew, is described.

2 Drawing Sheets

Genus and species: *Lagerstroemia indica.*
Variety denomination: 'JBG 19003'.

BACKGROUND

The present disclosure relates to a new and distinct cultivar of *Lagerstroemia* plant, commonly known as Crape Myrtle, a shrub that is grown for use as an ornamental landscape and container plant. The new variety is known botanically as *Lagerstroemia indica* and will be referred to hereinafter by the cultivar name 'JBG 19003'.

'JBG 19003' originated and was selected from a population of hybrid seedlings from a *Lagerstroemia* breeding program which was started in 2009. The breeding program was conducted at a nursery in Grand Saline, Tex. The aim of the breeding program is to develop new and improved genetics of dark leaf crape myrtles which exhibit high degrees of resistance to pests and diseases, together with high flower counts and the ability to reflower within each year. Varieties released from the breeding program are intended to be hardy, durable, and low maintenance for the consumer. 'JBG 19003' was selected in 2015 as a seedling from a group of seedlings from the open-pollination of a proprietary collection of dark-leaved *Lagerstroemia indica* varieties (unknown and unpatented). 'JBG 19003' was selected for its unique weeping and cascading plant habit when established, its bright red flowers, and its red-colored fall foliage.

'JBG 19003' was first asexually propagated in 2016 in a greenhouse nursery in Elk, Calif. using softwood cuttings. 'JBG 19003' has been confirmed to be stable and reproduces true to type in successive generations of asexual reproduction via softwood cuttings.

SUMMARY

The following traits have been repeatedly observed and represent the distinguishing characteristics of 'JBG 19003'.

'JBG 19003' has not been tested under all possible conditions and phenotypic differences may be observed with variations in environmental, climatic, and cultural conditions, without however, any variance in genotype.

1. 'JBG 19003' exhibits a compact plant habit.
2. The form of 'JBG 19003' is upright initially, becoming weeping or cascading when established and planted in the landscape.
3. The flowers of 'JBG 19003' are red in color.
4. The foliage of 'JBG 19003' is very dark brown to black in summer, and red-brown in color in the fall.
5. After one year's growth in a container, plants of 'JBG 19003' are 60 cm in height and 45 cm in width.
6. When established in the landscape, plants of 'JBG 19003' are 1.2 m in height and 1.5 m in width.
7. 'JBG 19003' is very well-adapted to heat, humidity and drought conditions.
8. 'JBG 19003' exhibits slight or occasional susceptibility to aphids, whitefly and powdery mildew.

DESCRIPTION OF THE PHOTOGRAPHS

The accompanying color photographs illustrate the overall appearance of *Lagerstroemia* cultivar 'JBG 19003' showing the colors as true as it is reasonably possible to obtain in colored reproductions of this type. The photographs were taken in July 2022 in Grand Saline, Tex. from a fifteen-month-old plant grown outdoors in a 2-gallon container, with one pinch after initial cutting establishment and without any chemical growth regulators. Colors in the photographs may differ from the color values cited in the detailed botanical description, which more accurately describes the actual colors of the new variety 'JBG 19003'.

DESCRIPTION OF THE NEW VARIETY

Figure 1:
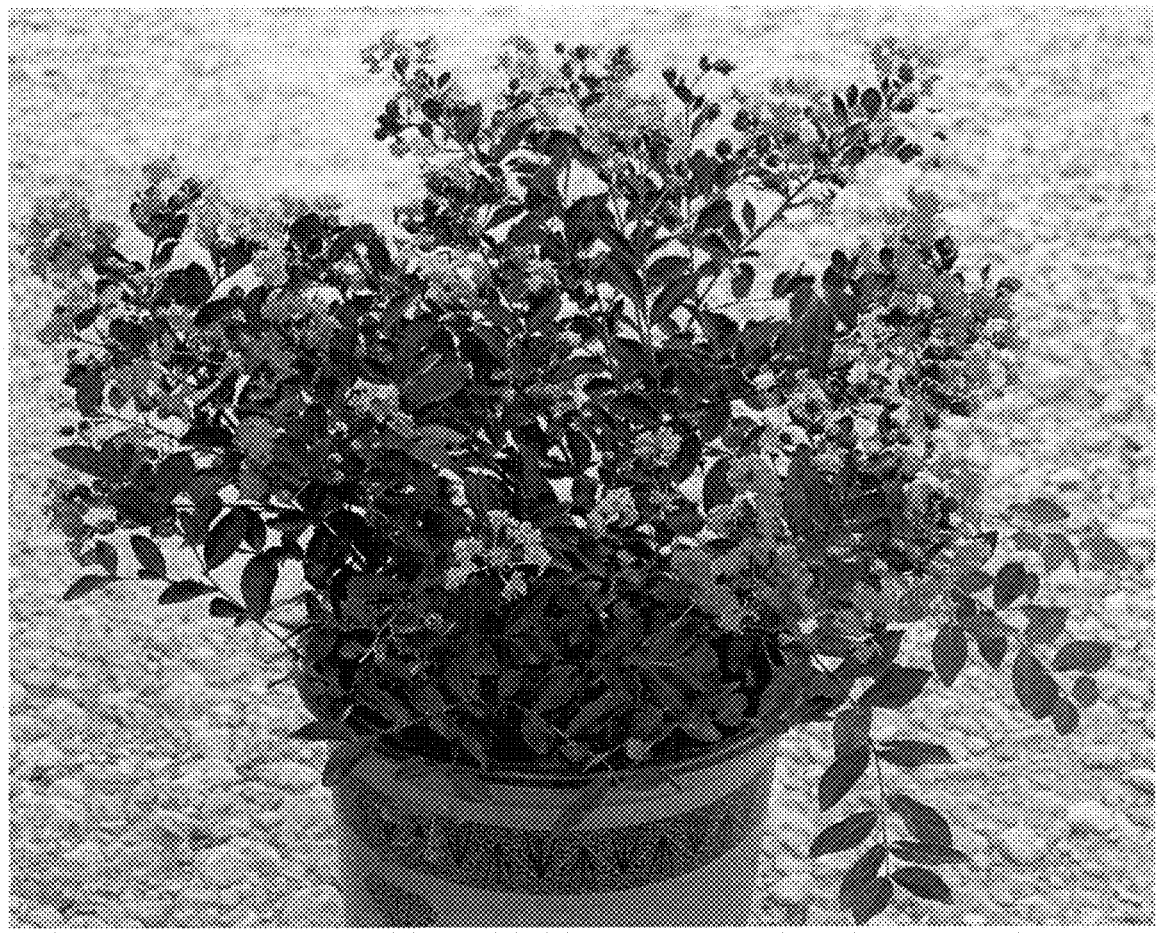
FIG. 1 depicts an entire plant in flower of 'JBG 19003'.
Figure 2:
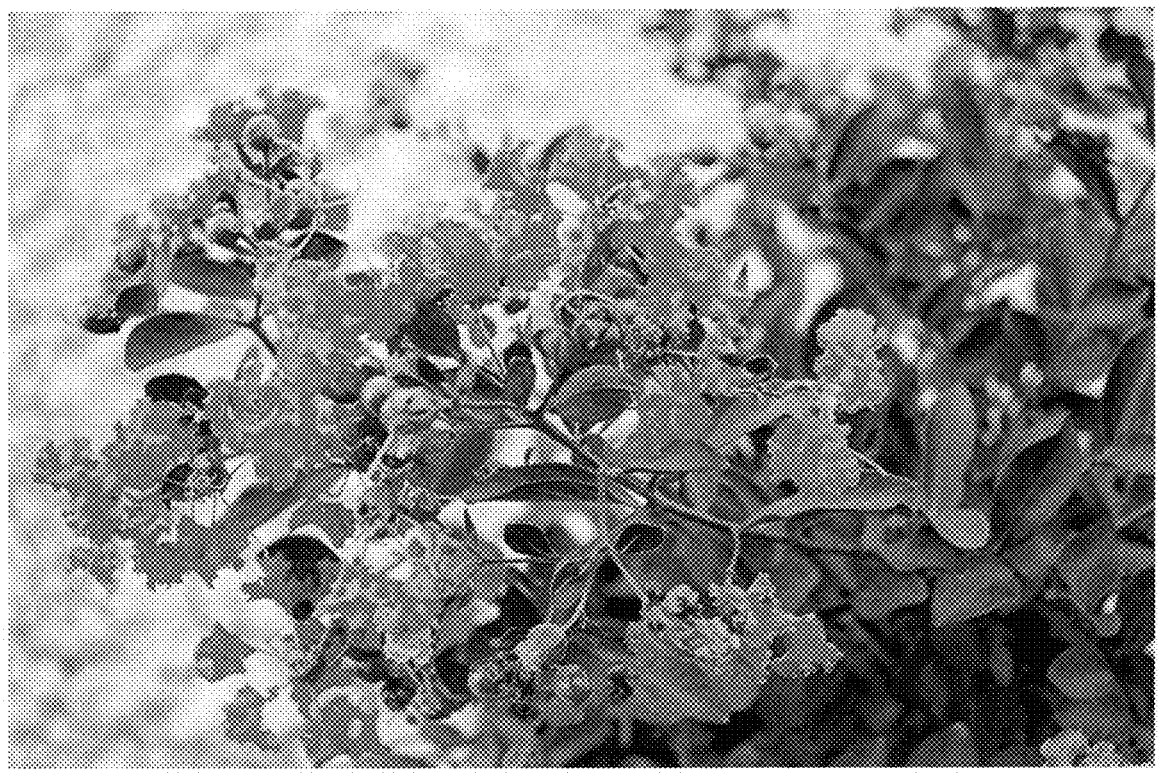
FIG. 2 depicts a close-up view of the inflorescence and flowers of 'JBG 19003'.

The following detailed descriptions set forth the distinctive characteristics of 'JBG 19003'. Observations, measurements, values, and comparisons were collected in July 2022 in Grand Saline, Tex. from a fifteen-month-old plant, growing outdoors in full sun in a 2-gallon container. Color determinations were made in accordance with The 2007 Royal Horticultural Society Colour Chart from London England, except where general color terms of ordinary dictionary significance are used.

Classification:

*Family*.—Lythraceae.

*Genus*.—*Lagerstroemia*.

*Species*.—*Indica*

*Common name*.—Crape Myrtle.

Parentage:

*Female parent*.—Unknown *Lagerstroemia indica* plant.

*Male parent*.—Unknown *Lagerstroemia indica* plant.

Plant:

*Propagation method*.—Softwood cuttings.

*Rooting system*.—Fine and fibrous, fresh new roots are 19D and older, more mature or established roots are 161C.

*Vigor*.—Moderate vigor.

*Time to develop roots*.—12 days are needed for a cutting to develop roots at recommended rooting temperature of 20° to 22° Centigrade.

*Crop time*.—Approximately 10 to 12 months are required to produce a budded and flowering plant in a 2-gallon container. Larger containers require a longer period of growth in order to fill out. Flowering will continue throughout spring, summer and fall.

*Suggested container sizes*.—2 gallon, 7-gallon.

*Use*.—Ornamental for use as a landscape plant or container plant.

*Type*.—Flowering shrub.

*Overall dimensions*.—After one year's growth in a container, plants of 'JBG 19003' are 60 cm in height and 45 cm in width. When well established in the landscape, plants of 'JBG 19003' are 1.2 m in height and 1.5 m in width.

*Cultural requirements*.—Grow in full-sun with moderate water and well-draining container medium or in well-draining sandy loam in the landscape.

*Hardiness*.—USDA Zone 6.

*Form*.—Initially upright becoming weeping and cascading when well established in the landscape.

*Growth habit*.—Compact.

*Blooming season*.—Continually and repeat flowering from late spring until fall.

*Lastingness of blooms*.—One week.

Stems (below first pinch):

*Shape*.—Round.

*Length*.—2 cm to 3 cm.

*Diameter*.—6 mm.

*Bark color*.—199B.

*Texture*.—Slightly rough or coarse.

Branches:

*Quantity*.—Approximately 40, of which 12 to 15 are primary branches and 25 or more are secondary branches.

*Branching habit*.—Freely branching, branches initially upright then weeping or cascading with age.

*Shape*.—Round.

*Length*.—Primary branches 45 cm to 50 cm to base of inflorescence; secondary branches 30 cm to 35 cm.

*Diameter*.—2 mm to 5 mm.

*Internode length*.—2.5 cm.

*Color* (*juvenile growth*).—184A.

*Color* (*mature growth*).—199B.

*Surface*.—Slightly rough.

*Strength*.—Firm and wiry.

Leaves:

*Type, arrangement*.—Simple, alternate.

*Attachment*.—Short petiolate.

*Quantity per branch*.—12 to 18.

*Shape*.—Elliptic.

*Length*.—3.0 cm.

*Width*.—1.6 cm.

*Margin*.—Entire.

*Aspect*.—Outward facing, angled towards apex.

*Texture* (*both surfaces*).—Smooth, glabrous.

*Glossiness of the adaxial surface*.—Medium.

*Color*.—Adaxial surface: 200A. Abaxial surface: 148A.

*Apex*.—Acute.

*Base*.—Acute.

*Venation*.—Pinnate.

*Veins* (*adaxial surface*).—Color 200B, raised above leaf surface.

*Veins* (*abaxial surface*).—Color 148A, raised above leaf surface.

Petiole:

*Shape*.—Cylindrical.

*Length*.—1 mm.

*Diameter*.—1 mm.

*Color*.—179B.

*Surface*.—Smooth, glabrous.

*Strength*.—Stiff and firm.

Peduncle:

*Description*.—Branches from each stem, subtends paniculate inflorescence.

*Shape*.—Cylindrical.

*Length*.—12 mm to 18 mm.

*Diameter*.—1.5 mm to 2.0 mm.

*Texture*.—Smooth.

*Color*.—183C.

Inflorescence:

*Type*.—Panicle.

*Length*.—8 cm to 10 cm.

*Width*.—9.5 cm.

Pedicels:

*Length*.—12 mm.

*Diameter*.—1 mm.

*Texture*.—Smooth.

*Color*.—183D.

Calyx:

*Shape*.—Campanulate.

*Height*.—7 mm.

*Diameter*.—9 mm.

Sepals:

*Quantity.*—6.
*Shape.*—Acutely triangular.
*Length.*—8 mm.
*Width at base.*—3 mm.
*Apex.*—Acute.
*Base.*—Obtuse.
*Margin.*—Entire.
*Texture* (*both surfaces*).—Smooth to very slightly rough.
*Color* (*both surfaces*).—182C.

Flowers:

*Quantity per plant.*—250 to 300 buds and flowers.
*Shape.*—Obovate.
*Fragrance.*—None.
*Width of individual flower.*—About 4.4 cm.

Bud:

*Shape.*—Globular to very slightly elongated.
*Dimensions.*—6 mm to 7 mm in height and diameter.
*Surface.*—Smooth.
*Color.*—178B.

Petals:

*Quantity.*—6.
*Arrangement.*—Free, rotate.
*Shape.*—Orbicular.
*Length.*—12 mm.
*Width.*—14 mm.
*Apex.*—Rounded.
*Base.*—Reniform.
*Margin.*—Smooth, undulating.
*Undulation of the petal.*—Strong.
*Color* (*both surfaces*).—61A.
*Texture* (*both surfaces*).—Smooth, glabrous.

Reproductive organs:

*Stamens, filaments.*—Quantity: 29. Arrangement: Upright tight cluster. Length: 10 mm. Diameter: 1 mm. Color: 155C.
*Anthers.*—Shape: Sulcate. Length: 2 mm to 3 mm. Width: 1.5 mm. Color: 23A.
*Pollen.*—Amount: Moderate. Color: 24A.
*Pistil.*—Quantity: 1. Dimensions: 8 mm in length, 2 mm in diameter.
*Stigma.*—Shape: Club shaped. Length: 1 mm. Diameter: 0.75 mm to 1 mm. Color: 147C.
*Ovary.*—Shape: Globular. Diameter: 2 mm. Color: 162D.

Seed: None observed to date.

Pest susceptibility: Slightly susceptible to aphids (*Aphis gossypii*) and occasionally to whitefly (*Trialeurodes vaporariorum*). In common with *Lagerstroemia* in general, 'JBG 19003' may become infected with crape myrtle bark scale (*Acanthococcus lagerstroemiae*).

Disease susceptibility: Slight incidence of powdery mildew (*Erysiphe lagerstroemia*).

Heat, humidity and drought tolerance: Very well adapted to heat, humidity and drought conditions.

COMPARISON WITH KNOWN VARIETY

When 'JBG 19003' is compared to the commercial *Lagerstroemia indica* variety 'Red Filli' (U.S. Plant Pat. No. 14,353), the form of 'JBG 19003' is upright initially, becoming weeping or cascading when established and planted in the landscape, while the form of 'Red Filli' is from spreading to flat spreading.

I claim:

1. A new and distinct cultivar of *Lagerstroemia* plant named 'JBG 19003' as described and illustrated herein.

* * * * *